United States Patent [19]

Oxenrider et al.

[11] 4,447,629

[45] May 8, 1984

[54] FLUORINATED AND NON-FLUORINATED SILOXY PYROMELLITATES

[75] Inventors: Bryce C. Oxenrider, Florham Park; David J. Long, Stanhope, both of N.J.

[73] Assignee: Allied Corporation, Morris Township, Morris County, N.J.

[21] Appl. No.: 429,946

[22] Filed: Sep. 30, 1982

[51] Int. Cl.$^3$ .............................. C07F 7/08; C07F 7/10; C07F 7/18

[52] U.S. Cl. .................................. 556/419; 556/429; 556/440; 428/375

[58] Field of Search ..................... 556/419, 429, 440

[56] References Cited

U.S. PATENT DOCUMENTS

| | | | |
|---|---|---|---|
| 2,802,853 | 8/1957 | George | 556/429 |
| 3,179,622 | 4/1965 | Haluska | 556/419 X |
| 3,288,754 | 11/1966 | Green | 556/419 X |
| 3,458,554 | 7/1969 | Haluska | 556/440 |
| 3,922,436 | 11/1975 | Bell et al. | 556/419 X |
| 4,192,754 | 3/1980 | Marshall et al. | 252/8.8 |
| 4,209,610 | 6/1980 | Mares et al. | 260/40 |

Primary Examiner—Paul F. Shaver
Attorney, Agent, or Firm—Alan M. Doernberg; Gerhard H. Fuchs; Kenneth E. Stroup

[57] ABSTRACT

Pyromellitate tetraesters are disclosed that are useful as water repellents. The pyromellitates of this invention characteristically contain two ester moieties wherein said ester moieties contain a fluorinated or saturated hydrocarbon alkyl group. Additionally, pyromellitates of this invention contain two ester moieties which contain siloxyl groups.

6 Claims, No Drawings

FLUORINATED AND NON-FLUORINATED SILOXY PYROMELLITATES

DESCRIPTION

Background Of The Invention

This invention relates to novel compounds synthesized from polycarboxy benzene dianhydrides. More specifically, the present invention relates to compounds synthesized by reacting fluorinated or hydrocarbon pyromellitate diester-diacid chlorides with siloxy amines. The compounds of the present invention are useful as water repelling agents.

Fluorinated pyromellitates and the use of such compounds as surface modifiers is disclosed in U.S. Pat. No. 4,209,610 (Mares et al., 1980). Mares et al. discloses various pyromellitate tetraesters wherein two ester moieties contain partially fluorinated alkyl groups and wherein two ester moieties contain alkyl groups substituted with a hydroxyl group or alkyl groups substituted with a halogen and a hydroxyl group. Mares et al. discloses a method for applying the compounds in organic solution to various fibers. A method for applying the compounds in an aqueous emulsion is disclosed in U.S. Pat. No. 4,192,754 (Marshall et al., 1980).

We have discovered that esterifying pyromellitic anhydride with fluorinated alcohols and siloxy amines or with hydrocarbon alcohols and siloxy amines results in compounds which are useful as water repellents.

BRIEF DESCRIPTION OF THE INVENTION

This invention relates to novel compounds having the structure:

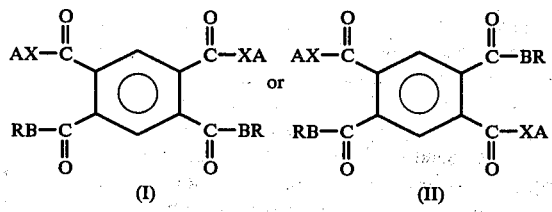

or mixtures thereof wherein X is —O—, —S—, —NH—, or —N(CH$_3$)—; wherein A is alkyl of 2-24 carbons or —R'—(CH$_2$)$_p$CF$_3$ with R' being alkylene of 1-6 carbons and p being an integer of 3-15; wherein B is —S—, —NH—, or —N(CH$_3$)— and where R is a monovalent radical of the formula —(CH$_2$)$_q$—Si(OR")$_3$, with q being an integer of 1 to 8, and R" being an alkyl group of 1 to 3 carbons.

The present invention also includes methods comprising applying the above composition to fibers such as polyester or polyamide fibers. Additionally, the invention includes polyester, polyamide, or other similar fibers having applied thereto the novel compounds described above.

DETAILED DESCRIPTION OF THE INVENTION

The novel compounds of the present invention are siloxy pyromellitates represented by the following general formulas:

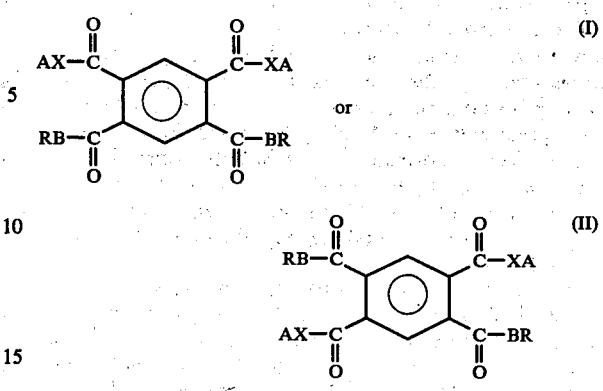

or mixtures thereof wherein X is —O—, —S—, —NH— or —N(CH$_3$)— with A being alkyl of 2 to 24 carbons or —R'—(CF$_2$)$_p$CF$_3$ where R' is alkylene of 1-6 carbons and p is an integer of 3-19; wherein B is —S—, —NH—, or —N(CH$_3$)— and where R is a monovalent radical of the structure —(CH$_2$)$_q$—Si(OR")$_3$, with q being an integer of 1-8, and R" being alkyl of 1-3 carbons.

The preferred siloxy pyromellitates are characterized by compounds wherein q is the integer 3, R" is an alkyl group of 1 or 2 carbons, and X is —O— in the above structures.

The pyromellitates of the present invention may be synthesized by initially reacting pyromellitic anhydride with fluoroalcohols in accordance with the procedures described in U.S. Pat. No. 4,209,610 in order to obtain a diester-diacid intermediate. Fluoroamines or fluorothiols may be used instead of fluoroalcohols in order to produce diamide-diacid or dithio-diacid intermediates. Alternately, hydrocarbon alcohols, amines, or thiols may be utilized in order to obtain non-fluorinated intermediate compounds. The intermediates thus obtained may then be converted to acid-chloride compounds by reacting the intermediates with a chlorinating agent such as oxalyl chloride, phosphorous pentachloride, phosgene-DMF, thionyl chloride or any other suitable chlorinating agent. This acid-chloride producing reaction should preferably be carried out at a temperature between room temperature and 60° C. under essentially anhydrous conditions. The synthesis of these acid-chlorides is discussed more fully in the copending commonly assigned application of Oxenrider and Long U.S. Ser. No. 429,947, filed Sept. 30, 1982. The final step of the synthesis involves reacting the diester-diacid chloride, diamide-diacid chloride or dithio-diacid chloride intermediate with a siloxy amine or siloxy thiol in the presence of a base to obtain a siloxy pyromellitate.

The siloxy pyromellitates are useful for applications in the general field of water repellents. In particular, it is expected that the pyromellitates of the present invention will have superior retention characteristics when applied to various fibers as opposed to the retention properties of previously known water repellents.

Application of the siloxy pyromellitates to fibers is accomplished in general by contacting such fibers with a liquid emulsion, dispersion or solution which contains siloxy pyromellitates, and thereafter usually heating said fibers sufficiently to develop soil and oil repellency. After use and cleaning (as approximated by standard laundering tests) the retention of water repellency is expected to be superior to known water repellents, due in part to the siloxy moiety.

The preferred fluorinated siloxy pyromellitates are those derived from fluorinated hydrocarbyl ethanols represented by the formula $CF_3(CF_2)_pCH_2CH_2O-$ where p is a commercial mixture of 3–15 or even larger, but is preferably 3–13. Slightly less preferred are those derived from fluorinated hydrocarbyl propanols and from fluorinated hydrocarbyl butanols. Substituents A with alkylenes of 1–6 carbons other than 1,2-ethylene, 1,2-propylene or 1–4-butylene may also be used, but are less preferred.

Hydrocarbon siloxy pyromellitates are also a subject of this invention. Hydrocarbon siloxy pyromellitates wherein A is alkyl of 2–24 carbons may be used in admixture with fluorocarbon siloxy pyromellitates in order to produce a less expensive water repellent.

Mixtures which consist essentially of hydrocarbon siloxy pyromellitates and fluorocarbon siloxy pyromellitates may be formed by simply dissolving the respective hydrocarbon and fluorocarbon siloxy pyromellitates in a common solvent to form a homogeneous solution. Suitable solvents for forming the solutions include chloroform, dioxane, acetone, and other similar solvents. These mixtures will have water repelling characteristics similar to solutions which contain only fluorinated compounds. However, these mixtures are less expensive to produce as the hydrocarbon diluent is not as expensive as the fluorocarbon component.

Fibers which have the compositions of the present invention applied thereto are also a subject of the present invention. Suitable fibers are polycaproamide, poly(hexamethylene diamine adipate) and poly(ethylene terphthalate) or other polyamides or other polyesters.

EXAMPLE 1

A mixture of meta and para isomers of the diester of pyromellitic anhydride and a mixture of fluorinated alcohols was prepared and isolated in accordance with the procedures of U.S. Pat. No. 4,252,982 to Oxenrider. This diester can be represented by the formulae:

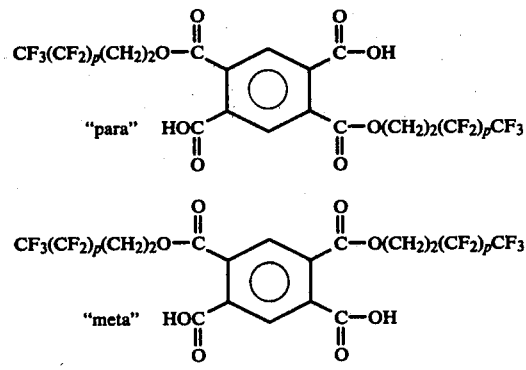

The values for p were 5, 7, 9 and 11 since a mixture of fluorinated alcohols had been used.

A portion of this mixture (10 g, 8.2 mmol) was suspended in ethyl acetate (50 mL) under nitrogen at 45° C. in a 100 mL round bottom flask. A solution of oxalyl chloride (1.5 mL, 17 mmol) in dry ethyl acetate was prepared and added to the suspended diester-diacid. The resultant reaction mixture was stirred for 3 hours at 50° C. At this stage of the reaction the diester-diacid has now been converted to a diester-diacid chloride which is in solution. A mixture of N-methyl-N-trimethoxysilylpropylamine (4.0 g, 21 mmol) and pyridine (1.4 mL) in ethyl acetate (10 mL) was added to the diester-diacid cloride solution. This reaction mixture was stirred at 45°–50° C. for 1 hour, cooled to room temperature, filtered, and evaporated on a rotary evaporator. A semi-solid product (11.6 g) was obtained and confirmed by proton NMR to be a siloxy pyromellitate. The product had an oil repellency of 4 as determined by AATCC procedures.

EXAMPLE 2

A portion of the mixture of meta and para pyromellitate diacid-diesters (5 g, 8.585 meq) of Example 1 and dry ethyl acetate (20 mL) were added to a 100 mL round bottom flask to form a suspension. The suspension was warmed to 45° C. and then a solution of oxalyl chloride (0.8 mL, 8.585 meq) and dry ethyl acetate (10 mL) was added over a period of 20 minutes. The solution was stirred and the reaction was allowed to continue for a period of 4 hours at a temperature of 45° C. in order to produce a diester-diacid chloride.

A separate reactant mixture of mercaptopropyltriethoxysilane (1.88 g, 8.585 meq), triethyl amine (6.65 mL) and dry ethyl acetate (20 mL) was prepared. The diester-diacid chloride product solution was added to this reactant mixture over a period of 20 minutes. The resultant product solution was stirred at 45° C. for 2 hours and then stirred overnight at room temperature. The product solution was filtered and flash evaporated and 3.5 g of a yellow-orange viscous liquid product was recovered. The structure of the siloxy pyromellitate was confirmed by proton NMR. The surface energy of the siloxy pyromellitate was determined to be 14 dynes/cm by the Zisman technique.

EXAMPLE 3

PERFORMANCE EVALUATION

The water repellency and retention of water repelling properties by fibers treated with the compounds of this invention were evaluated by subjecting the fibers to agitation in a standard laundrometer and then performing a water repellency test upon the fibers. The results were compared with those of a fiber which was not subjected to agitation. In order to obtain this data, a solution was prepared by dissolving about 0.25 g of a product prepared in accordance with Example 2 in about 100 mL of acetone. Swatches of knitted sleeve fabric made from nylon 6 fiber (about 15 denier) were dipped in the solution and then air dried. This procedure imparted about 476 ppm fluorine to the swatches of fabric. The treated fabric swatches were placed in laundrometer testing containers which contained 150 mL of a test solution per 5 g of knitted sleeve fabric. The test solution was comprised of 0.25% owm Chemco Antifoam, 2.0% owm Alkanol ND, 2.0% owm sodium phosphate (monobasic), and a sufficient amount of sodium phosphate (tribasic) so that the pH of the test solution was about 6.5. The containers were placed in a standard laundrometer which was filled with cold water. Agitation of the treated fabrics was accomplished by running the laundrometer for a number of cycles. A cycle consisted of operating the laundrometer at 42 rpm and supplying sufficient heat so that the temperature of the water in the laundrometer reached 100° C. after 1 hour. Fabric swatches which were subjected to 1, 3, and 5 cycles were removed from the test containers, rinsed in lukewarm tap water, hydroextracted, and air dried. These fabric swatches in addition to a fabric swatch which had not been subjected to agitation in the laundrometer were then tested for water repellency.

Water repellency testing was accomplished by placing a drop of the test solutions which are characterized in the table hereinbelow on the fabric swatches. If the drop was not absorbed by the fabric after 30 seconds, the fabric was considered to be water repellent with respect to the test solution employed.

A water repellency rating of 4 or 5 (i.e. with respect to test solution 4 or 5) is very good. The test solutions are characterized in the following table:

| Test Soln. | Volume % | | Surface Tension |
| --- | --- | --- | --- |
| | isopropanol | water | (dynes/cm) |
| #1 | 2 | 98 | 55 |
| #2 | 5 | 95 | 47 |
| #3 | 10 | 90 | 40 |
| #4 | 20 | 80 | 33 |
| #5 | 30 | 70 | 28 |

Fabric swatches which had been subjected to 0, 1, 3, and 5 cycles of laundrometer agitation were evaluated for water repellency with the test solutions in the above table. All four samples exhibited a water repellency rating of 4 (i.e. with respect to test solution #4). Thus, the compounds of this invention impart water repelling properties to fibers, and the water repelling properties are retained by the fibers after extensive laundering.

We claim:

1. A monocyclic compound having the structure:

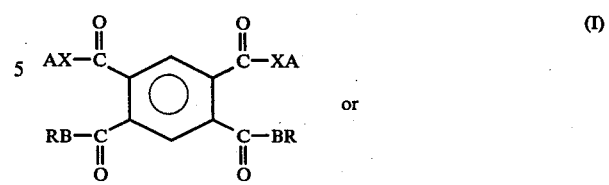

or

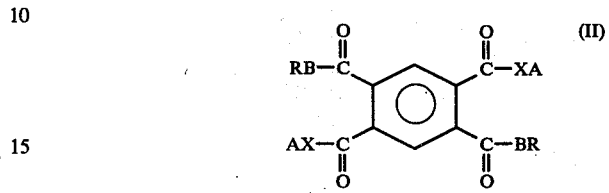

or mixtures thereof wherein X is independently at each occurrence —O—, —S—, —N(CH$_3$)— or —NH—; wherein A is alkyl of 2-24 carbons or R'—(CF$_2$)$_p$CF$_3$ with R' being alkylene of 1-6 carbons and p being an integer of 3-15; wherein B is —S—, —NH—, or —N(CH$_3$)— and where R is a monovalent radical of the structure —(CH$_2$)$_q$—Si(OR")$_3$, with q being an integer of 1 to 8, and R" being alkyl of 1-3 carbons.

2. The compound of claim 1 wherein q is 3.

3. The compound of claim 2 wherein X is —O—.

4. The compound of claim 3 wherein A is (CH$_2$)$_2$(CF$_2$)$_p$CF$_3$ and p is an integer of 3 to 13.

5. The compound of claim 4 wherein R" is methyl.

6. The compound of claim 4 wherein R" is ethyl.

* * * * *